US009901619B2

(12) United States Patent
Shalgi et al.

(10) Patent No.: US 9,901,619 B2
(45) Date of Patent: *Feb. 27, 2018

(54) COMPOSITIONS COMPRISING PEDF AND USES OF SAME IN THE TREATMENT AND PREVENTION OF OVARY-RELATED SYNDROMES

(71) Applicants: Ramot at Tel-Aviv University Ltd., Tel-Aviv (IL); The Fund for Medical Research, Development of Infrastructure and Health Services—Assaf HaRofeh Medical Center, Zerifin (IL)

(72) Inventors: Ruth Shalgi, Herzlia (IL); Dana Chuderland, Ramat-HaSharon (IL); Ido Ben-Ami, Tel-Aviv (IL); Raphael Ronel, Yahud (IL)

(73) Assignees: Ramot at Tel-Aviv University Ltd., Tel-Aviv (IL); The Fund for Medical Research, Development of Infrastructure and Health Services—Assaf HaRofeh Medical Center, Zerifin (IL)

( * ) Notice: Subject to any disclaimer, the term of this patent is extended or adjusted under 35 U.S.C. 154(b) by 159 days.

This patent is subject to a terminal disclaimer.

(21) Appl. No.: 14/628,312

(22) Filed: Feb. 23, 2015

(65) Prior Publication Data
US 2015/0164989 A1    Jun. 18, 2015

Related U.S. Application Data

(63) Continuation of application No. 13/509,622, filed as application No. PCT/IL2010/000936 on Nov. 11, 2010, now Pat. No. 8,962,561.

(60) Provisional application No. 61/260,415, filed on Nov. 12, 2009.

(51) Int. Cl.
A61K 38/18 (2006.01)
A61K 38/57 (2006.01)
A61K 38/24 (2006.01)

(52) U.S. Cl.
CPC .............. *A61K 38/18* (2013.01); *A61K 38/24* (2013.01); *A61K 38/57* (2013.01)

(58) Field of Classification Search
None
See application file for complete search history.

(56) References Cited

U.S. PATENT DOCUMENTS

| 8,530,416 B2 | 9/2013 | Seger et al. |
| 2003/0216286 A1 | 11/2003 | Bouck et al. |
| 2004/0014664 A1 | 1/2004 | Bouck et al. |
| 2004/0161423 A1 | 8/2004 | Kumar |
| 2006/0189519 A1 | 8/2006 | Volz et al. |
| 2008/0274967 A1 | 11/2008 | Maik-Rachline et al. |
| 2013/0053312 A1 | 2/2013 | Shalgi et al. |

FOREIGN PATENT DOCUMENTS

| CH | WO2005/027973 | * 3/2005 | ............. A61K 45/06 |
| WO | WO 2007/033215 | 3/2007 | |
| WO | WO 2008/085828 | 7/2008 | |

OTHER PUBLICATIONS

Al-Azemi et al., Human Reproduction, 2000; 15: 72-75.*
Petraglia et al., Best Practice & Research Clinical Obstetrics and Gynaecology, 2008; 22: 235-249.*
Chuderland et al., Human Reproduction, 2013; 28: 1626-1634.*
Becker et al., Microvascular Research, 2007; 74: 121-130. (Year: 2007).*
Huang et al., European Journal of Obstetrics & Gynecology and Reproductive Biology, 2012; 165: 104-109. (Year: 2012).*
The website WebMD, https://www.webmd.com/drugs/condition-3458-Stimulation+of+Ovarian+Function.aspx?diseaseid=3458&diseasename=Stimulation+of+Ovarian+Functi . . . ; 3 pages total, downloaded Nov. 13, 2017 (Year: 2017).*
Communication Pursuant to Article 94(3) EPC dated Aug. 9, 2013 From the European Patent Office Re. Application No. 10790997.0.
Communication Pursuant to Article 94(3) EPC dated Mar. 11, 2013 From the European Patent Office Re. Application No. 10790997.0.
Communication Pursuant to Article 94(3) EPC dated Feb. 28, 2014 From the European Patent Office Re. Application No. 10790997.0.
International Preliminary Report on Patentability dated May 24, 2012 From the International Bureau of WIPO Re. Application No. PCT/IL2010/000936.
International Search Report and the Written Opinion dated Mar. 1, 2011 From the International Searching Authority Re. Application No. PCT/IL2010/000936.
Official Action dated Jul. 2, 2014 From the US Patent and Trademark Office Re. U.S. Appl. No. 13/509,622.
Official Action dated Feb. 19, 2014 From the US Patent and Trademark Office Re. U.S. Appl. No. 13/509,622.
Restriction Official Action dated Dec. 20, 2013 From the US Patent and Trademark Office Re. U.S. Appl. No. 13/509,622.

(Continued)

*Primary Examiner* — Christina M Borgeest

(57) ABSTRACT

A method of treating or preventing an ovary-related syndrome associated with infertility in a subject in need thereof is provided. The method comprising administering to the subject a pharmaceutical composition comprising an active ingredient consisting of pigment epithelium-derived factor (PEDF) and a pharmaceutically acceptable carrier, thereby treating or preventing the ovary-related syndrome associated with infertility in the subject.

10 Claims, 6 Drawing Sheets (5 of 6 Drawing Sheet(s) Filed in Color)

(56) References Cited

OTHER PUBLICATIONS

Becker et al. "Angiogenesis and Antiangiogenic Therapy in Endometriosis", Microvascular Research, XP022334277, 74(2-3): 121-130, Sep. 1, 2007. Abstract.
Ben-Ami et al. "Novel Treatment for Ovarian Hyperstimulation Syndrome (OHSS) Using Pigment Epithelium Derived Factor (PEDF)", Abstracts of the 27th Annual Meeting of the European Society of Human Reproduction and Embryology, ESHRE, Stockholm, Sweden, Jul. 3-6, 2011, Selected Oral Communication Session, Session 25: # O-093, P.i37-i38, 2011.
Brinton et al. "Ovarian Cancer Risk Associated With Varying Causes of Infertility", Fertility and Sterility, 82(2): 405-414, Aug. 2004.
Casper "Aromatase Inhibitors in Ovarian Stimulation", The Journal of Steroid Biochemistry & Molecular Biology, 106: 71-75, 2007.
Chen et al. "Decreased Concentrations of Pigment Epithelium-Derived Factor in Peritonal Fluid of Patients With Endometriosis". Fertility and Sterility, XP009144704, 95(5): 1798-1800, Apr. 2011.
Chuderland et al. "The Role of Pigment Epithelium-Derived Factor in the Pathophysiology and Treatment of Ovarian Hyperstimulation Syndrome in Mice", Journal of Endocrinology & Metabolism, 98(2): E258-E266, Feb. 2013.
Dawson et al. "Pigment Epithelium-Derived Factor: A Potent Inhibitor of Angiogenesis", Science, 285: 245-248, Jul. 9, 1999.
Pal et al. "Impact of Varying Stages of Endometriosis on the Outcome of in Vitro Fertilization-Embryo Transfer", Journal of Assisted Reproduction and Genetics, 15(1): 27-31, 1998.
Plunkett et al. "Decreased Expression of Pigment Epithelium Derived Factor (PEDF), An Inhibitor of Angiogenesis, in Placentas of Unexplained Stillbirths", Reproductive Biology, XP002622497, 8(2): 107-120, Jul. 2008. Introduction.
Steinkamp et al. "Assisted Reproduction in Patients With Early-Stage Ovarian Malignancies", Fertility and Sterility, 80(6): 1510-1512, Dec. 2003.
Tombran-Tink et al. "Therapeutic Prospects for PEDF: More Than A Promising Angiogenesis Inhibitor", Trends in Molecular Medicine, 9(6): 244-250, Jun. 2003.

* cited by examiner

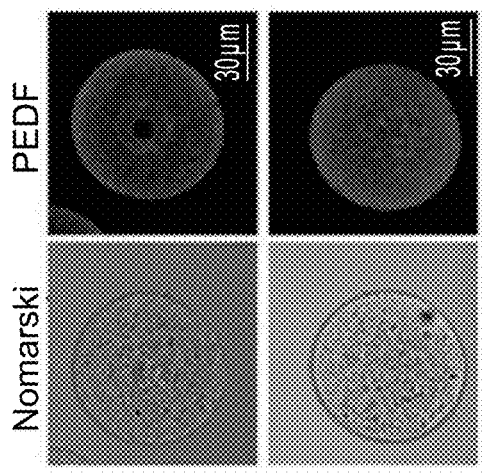
FIG. 1A
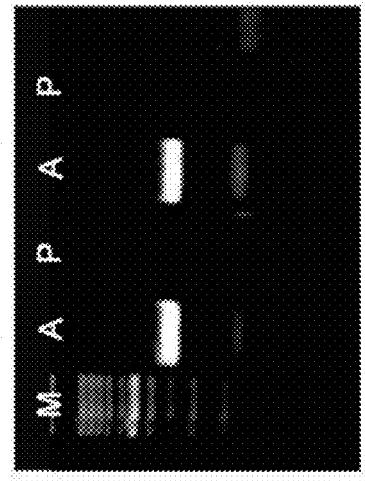
FIG. 1B
FIG. 1C
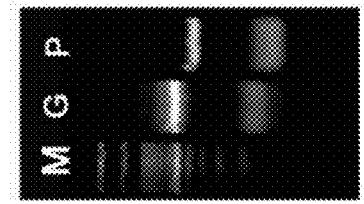
FIG. 1D

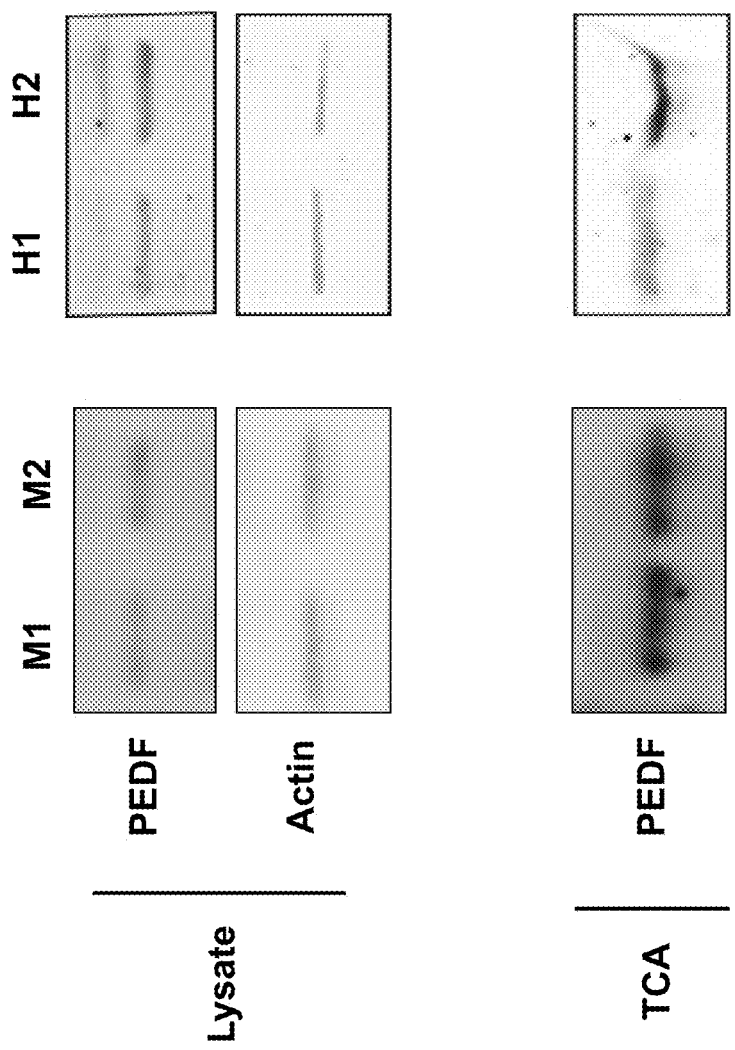

COMPOSITIONS COMPRISING PEDF AND USES OF SAME IN THE TREATMENT AND PREVENTION OF OVARY-RELATED SYNDROMES

RELATED APPLICATIONS

This application is a continuation of U.S. patent application Ser. No. 13/509,622 filed on Nov. 15, 2012, which is a National Phase of PCT Patent Application No. PCT/IL2010/000936 having International filing date of Nov. 11, 2010, which claims the benefit of priority under 35 USC 119(e) of U.S. Provisional Patent Application No. 61/260,415 filed Nov. 12, 2009, the contents of which are incorporated herein by reference in their entirety.

SEQUENCE LISTING STATEMENT

The ASCII file, entitled 60885SequenceListing.txt, created on Feb. 16, 2015, comprising 35,328 bytes, submitted concurrently with the filing of this application is incorporated herein by reference.

FIELD AND BACKGROUND OF THE INVENTION

The present invention, in some embodiments thereof, relates to compositions comprising PEDF and uses of same in the treatment and prevention of ovary-related syndromes.

Unlike any other organ, the female reproductive organs (i.e., ovary, uterus, and placenta) exhibit cyclic regulation of angiogenesis [1]. In the ovary, regulation of angiogenesis is critical for achieving a healthy mature oocyte. During folliculogenesis, the primordial and primary follicles are avascular and receive nutrients and oxygen by passive diffusion from stromal blood vessels. The vascular sheath that develops around each follicle is confined to the theca cells layer, whereas the granulosa cells remain avascular until ovulation, isolated from direct blood supply by the "blood follicular barrier". Thus, the maturing follicle remains avascular before ovulation, implying that regulatory mechanism must be present to prevent premature follicular vascularization.

Studies showed that culture media, conditioned by theca cells, stimulate proliferation and migration of endothelial cells regardless of the developmental stage of the follicle. However, Granulosa cells from early follicular phase inhibited migration and proliferation of endothelial cells, while towards ovulation, prior to becoming part of the highly vascular corpus luteum (CL) [3], they stimulated migration and proliferation of endothelial cells [4].

To date, extensive research has been performed to characterize pro-angiogenic factors in the ovary. Indeed, vascular endothelial growth factor (VEGF) and fibroblast growth factor 2 (FGF2) were shown to play an important role in the regulation of ovarian angiogenesis. However, only very few studies were conducted to find follicular anti-angiogenesis factors that prevent vessels penetration during folliculogenesis [5].

Ovarian stimulation is used with the intention of retrieving a high number of oocytes in order to improve the outcome of assisted reproductive treatments. However, administration of high doses of exogenous gonadotropins may lead to ovarian hyperstimulation syndrome (OHSS). This syndrome appears to be induced by the ovarian release of vasoactive-angiogenic substances which results in vascular hyperpermeability, leakage and shift of fluids from blood vessels into the extravascular space leading to consequent clinical manifestations including ascites and edema. Since severe OHSS is potentially life-threatening, that can occur in an otherwise healthy young women undergoing fertility treatments, much effort is made to prevent this iatrogenic complication. VEGF was recently pointed out as a crucial protein participating in the development of OHSS (reviewed in [6]) and the inhibition of the VEGF system could prevent OHSS from occurring. For example, Bevacizumab (Avastin™), a humanized monoclonal antibody that recognizes and blocks vascular endothelial growth factor A was suggested as the premium treatment [7]. However, serious adverse have been reported such as bowel perforation, heart attack and stroke.

In a similar manner to the ovarian follicle, the endometrium also undergoes cyclical changes in the course of the ovulatory cycle. Angiogenesis is reinitiated in the uterus during the follicular phase and continues through the luteal phase of the menstrual cycle due to hormonal induction[1]. In both in vivo and in vitro human models, it has been demonstrated that endometrial angiogenesis is regulated by VEGF, and its expression is significantly increased by estradiol (E2) and progesterone (P) [8].

Endometriosis is a pathological condition characterized by ectopic endometrial implants, commonly in the peritoneal cavity. Active endometriosis is characterized by hypervascularization both within and surrounding the implant. A higher VEGF level has been observed in the peritoneal fluid of patients with endometriosis and its production is stimulated by both E2 and P [8].

Pigment epithelium-derived factor (PEDF) is a non-inhibitory member of the serine protease inhibitors (serpin) superfamily, which was first described as a neurotrophic factor, able to promote and support the growth of neuronal cells [9]. However, it was later shown that besides its neurotrophic function, PEDF is also a potent, natural inhibitor of angiogenesis [10]. Importantly, its anti-angiogenic activity is far greater than that of any other known endogenous factor. The anti-angiogenic effect of PEDF has been extensively investigated in the eye, demonstrating its role in decreasing abnormal neovascularization, mainly by inhibiting the stimulatory activity of several strong pro-angiogenic factors, such as VEGF [11]. Although originally discovered in culture media of retinal pigment epithelial cells, PEDF is widely expressed throughout the body: the nervous system, ovary, uterine, liver [12] and plasma [13]. Despite the significant expression of PEDF in the reproductive system, there is only limited data about its function in the ovary [14] and uterus [15, 16] referring mainly to regulation in cancer.

U.S. Patent Application Number 20080274967 relates to the use of phosphorylated PEDF for the treatment of ovarian cancer.

U.S. Patent Application Numbers 20030216286 and 20040014664 teaches the use of PEDF for inhibiting ovarian and endometrial neovascularization such as for use as a contraceptive by attenuating neovascularization associated with ovulation, implantation of an embryo and placenta formation.

International Patent Publication Number WO2007033215 teaches anti-angiogenic compositions for the treatment of endometriosis and ovarian hyperstimulation.

U.S. 20040161423 teaches polymer modified PEDF for the treatment of endometriosis.

SUMMARY OF THE INVENTION

According to an aspect of some embodiments of the present invention there is provided a method of treating or preventing an ovary-related syndrome associated with infertility in a subject in need thereof, the method comprising administering to the subject a pharmaceutical composition comprising an active ingredient consisting of pigment epithelium-derived factor (PEDF) and a pharmaceutically acceptable carrier, thereby treating or preventing the ovary-related syndrome associated with infertility in the subject.

According to some embodiments of the invention, the ovary-related syndrome associated with infertility is selected from the group consisting of ovarian hyperstimulation, endometriosis, infertility and polycystic ovarian syndrome According to some embodiments of the invention, the subject is treated with an ovarian stimulating medication.

According to some embodiments of the invention, the ovarian stimulating medication comprises gonadotropin stimulation.

According to some embodiments of the invention, when the ovary-related syndrome associated with infertility is ovarian hyperstimulation, the administering is effected at the acute phase of the hyperstimulation.

According to some embodiments of the invention, when the ovary-related syndrome associated with infertility is ovarian hyperstimulation the administering is effected concomitant with the ovarian stimulating medication administration.

According to some embodiments of the invention, when the ovary-related syndrome associated with infertility is polycystic ovarian syndrome, the administering is effected prior to and/or concomitant with the gonadotropin stimulation at the follicular phase.

According to some embodiments of the invention, when the ovary-related syndrome associated with infertility is endometriosis, the administering is chronic.

According to some embodiments of the invention, administering is effected at a dosage range of 0.02-0.4 mg/kg.

According to some embodiments of the invention, the administering is effected at a dosage range of 0.162-0.32 mg/kg.

According to an aspect of some embodiments of the present invention there is provided a pharmaceutical composition comprising an active ingredient consisting of PEDF for use in the treatment or prevention of an ovary-related syndrome associated with infertility.

According to an aspect of some embodiments of the present invention there is provided a unit dosage form comprising 1-25 mg PEDF.

According to an aspect of some embodiments of the present invention there is provided a unit dosage form comprising 9-20 mg PEDF.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are images showing the expression of PEDF in the ovary. FIG. 1A—Histological sections of mouse ovaries labeled with anti PEDF antibody and Hoechst as a nuclear marker. PEDF is observed within the follicle in the oocyte and the granulosa cells (arrow). Lower panel describes higher magnification of the follicle. FIG. 1B—Freshly isolated, ovarian GV (germinal vesicle) oocytes (top, synchronized mice treated with 5 IU PMSG) and ovulated MII oocytes (bottom; from PMSG (5 IU) and hCG (7 IU) superovulated mice) labeled with anti PEDF antibody. PEDF is produced only by granulosa cells FIGS. 1C-D—Autoradiograph of a representative PCR analysis (X35 cycles) demonstrating expression of PEDF mRNA (P). FIG. 1C—primary granulosa cells obtained from follicles of 27 days old ICR mice after 3 days of estrogen administration and cultured for additional 7 days before mRNA extraction. Control (GAPDH primers—G). Marker (M). FIG. 1D—Extraction of mRNA from batches of 100 oocytes, demonstrating lack of PEDF mRNA (P) expression in ovarian GV oocytes and ovulated MII oocytes. Control (actin primers—A); marker (M).

FIGS. 2A-B are images showing that PEDF is expressed and secreted by granulosa cells. Primary granulosa cells were cultured for 7 days to reach hormonal quiescence; Western blot analysis was effected with a specific PEDF antibody; cell lysates were calibrated with Actin antibody (Two upper panels) and TCA precipitation (Lower panel). FIG. 2A—Primary granulosa cells obtained from follicles of 27 days old ICR mice after 3 days of estrogen administration. FIG. 2B—Human primary granulosa cells (Helsinki 167/09) harvested from follicles of women undergoing IVF treatment.

Figure 3A:
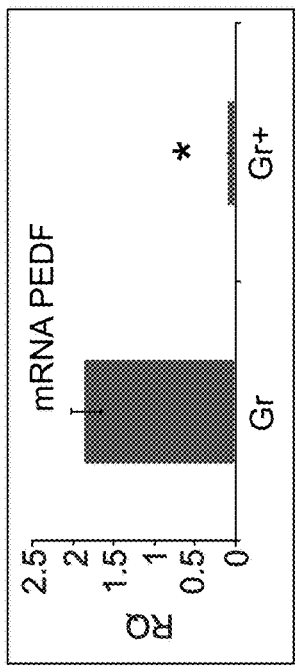
Figure 3B:
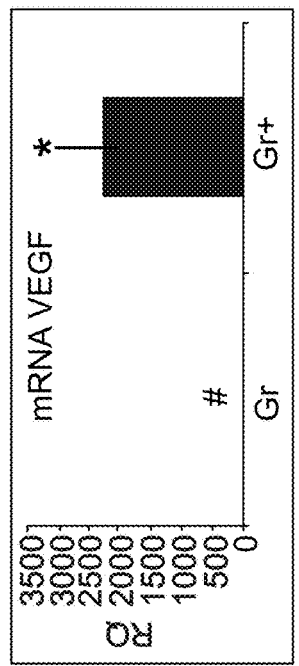
Figure 3D:
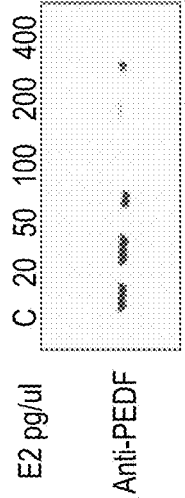
Figure 3E:
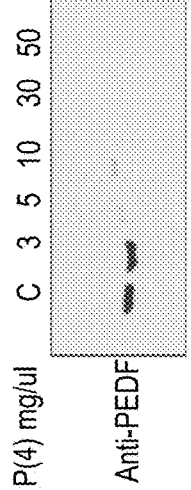
Figure 3C:
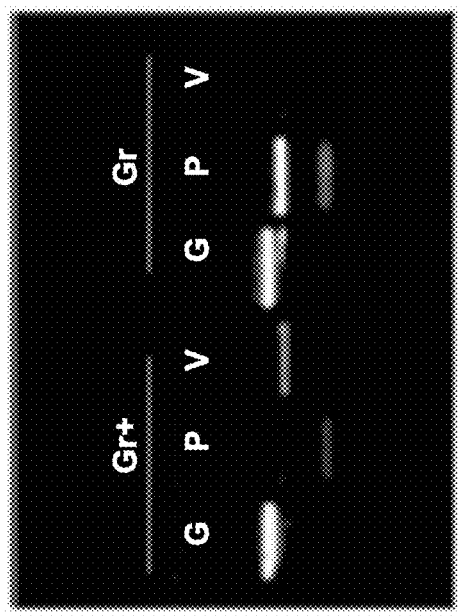

FIGS. 3A-E show hormonal regulation of PEDF and VEGF in an opposing manner. PEDF and VEGF expression in primary granulosa cells before and after ovulation is shown in FIGS. 3A-B. Granulosa cells were isolated from follicles of PMSG (5 IU) primed, 7 weeks old ICR mice (Gr) or from oviductal ampullae of superovulated 7 weeks old ICR mice (5 IU PMSG; 7 IU hCG); (Gr+). FIG. 3A—Autoradiograph of a representative semi-quantitative PCR analysis (X35 cycles) of primary mouse granulosa cells of PEDF (P) and VEGF (V) mRNAs occurring after in vitro hCG stimulation. Control (GAPDH primers—G). FIG. 3B—RNA extracted from primary granulosa cells that were subjected to qPCR analysis with specific primers for PEDF and VEGF and calibrated with the endogenous control HPRT1. Bars represent Mean±SEM, 6 mice/treatment, (*)—significantly different from control value (P<0.05; T test). The effect of hCG on primary human granulosa cells is shown in FIG. 3C—Human primary granulosa cells (Helsinki 167/09) were harvested from follicles of women undergoing IVF treatment. IVF protocol includes stimulation with hCG to induce ovulation and oocyte retrieval 36 hrs later. These primary granulosa cells were cultured for additional 5-10 days post hCG administration. TCA precipitation was performed from culture media on each day between days 5-10. PEDF proteins were detected using WB analysis with specific antibody. FIGS. 3D-E show that Estrogen and Progesterone downregulate PEDF. TCA precipitation of conditioned media of human primary granulosa cells that were pre-cultured for 7 days to reach hormonal quiescence and treated with increasing amount of Estrogen (E2) and Progesterone (P). PEDF proteins were detected using Western blot analysis with a specific antibody.

Figure 4A:
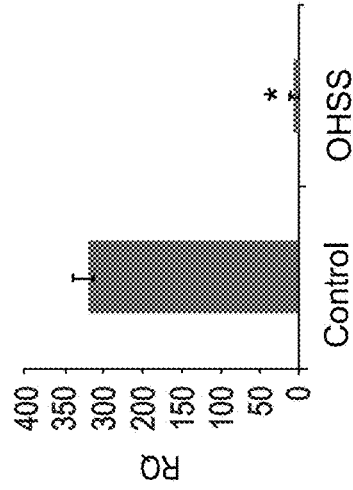
Figure 4B:
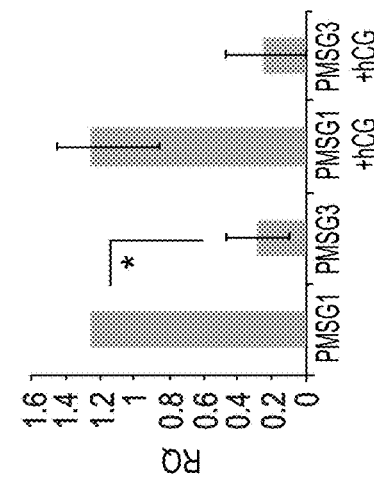
Figure 4C:
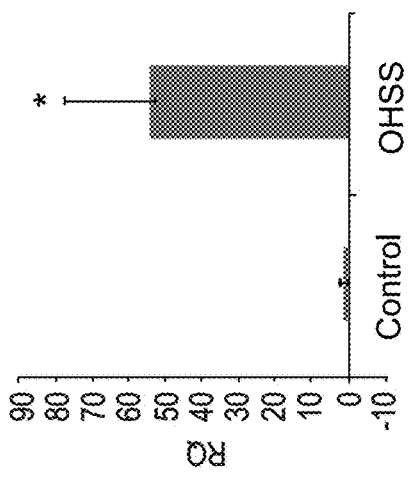
Figure 4D:
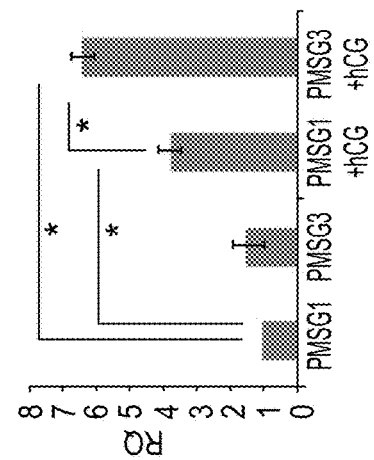

FIGS. 4A-D are graphs showing that induction of OHSS reduces PEDF levels. Excess gonadotropins alters the production of ovarian PEDF and VEGF (FIGS. 4A-B). Ovarian hyperstimulation syndrome (OHSS) was induced in 5 weeks ICR female mice by 3 consecutive daily injections of PMSG (20 IU) followed 24 hours later by hCG (7 IU) stimulation (OHSS). The control group was administrated with PMSG (5 IU), followed by hCG (7 IU) 48 hours later (control). Animals were scarified 48 hr after hCG administration, ovaries excised and ovarian mRNA was extracted. qPCR analysis with specific primers for VEGF (FIG. 4A) and PEDF (FIG. 4B) was performed and calibrated by the endogenous control HPRT1. Bars represent Mean±SEM, 10 mice/treatment, (*)—significantly different from control value ($P<0.05$; T test). Changes in the balance between PEDF and VEGF in granulosa cells are shown in FIGS. 4C-D. Granulosa cells were obtained from 5 weeks ICR mice as follow: (I) Single treatment of PMSG (5 IU; PMSG1); (II) administration of PMSG (20 IU) for sequential 3 days (PMSG3); (III) administrating of hCG (7 IU) after signal treatment of PMSG (5 IU; PMSG1+hCG), and (IV) 3 sequential days of PMSG (20 IU) followed by hCG (7 IU; PMSG3+hCG). Subsequently, cells were subjected to RNA extraction and qPCR analysis using specific primers for VEGF and PEDF and calibrated by endogenous control HPRT1. Bars represent Mean±SEM, 8 mice/group, (*)—significantly different from control value ($P<0.05$; Ttest and Mann-Whitney).

FIGS. 5A-D show that PEDF can be used as a treatment for OHSS.

Figure 5A:
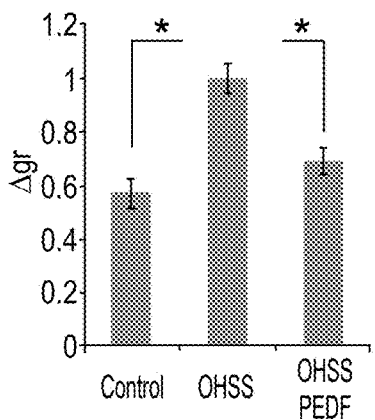
Figure 5B:
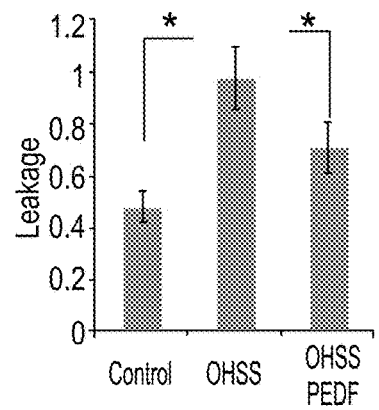
Figure 5C:
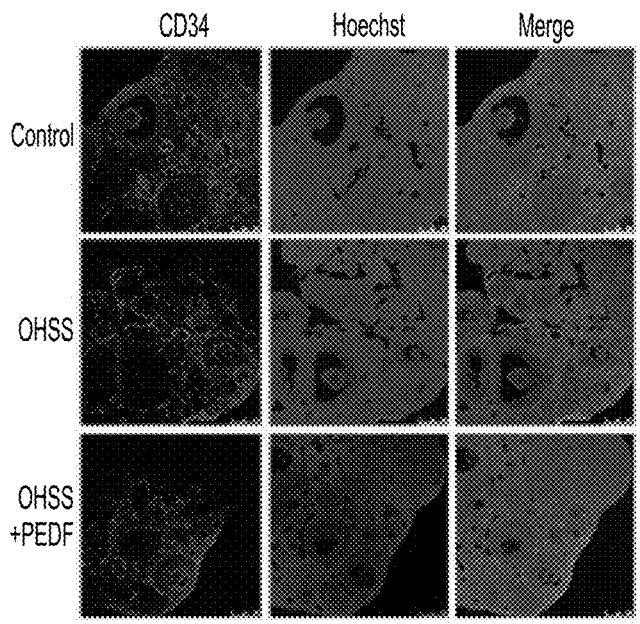
Figure 5D:
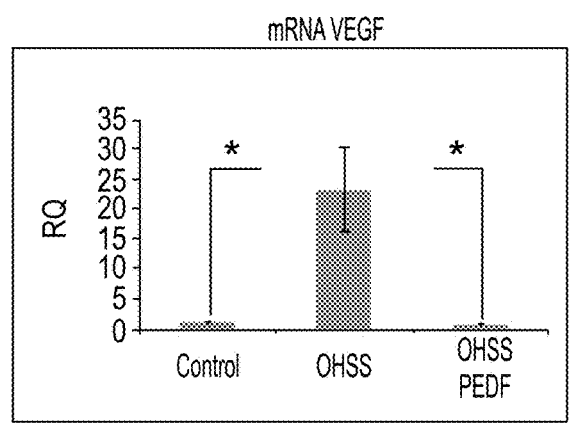

(I) ovarian hyperstimulation syndrome (OHSS) was induced in female mice by 3 consecutive daily injections of PMSG (20 IU) followed 24 hours later by hCG (7 IU) (OHSS) along with intravenously injections of PBS on day 1 and 3 of PMSG stimulation. (II) OHSS+PEDF: Mice were injected with PEDF (2 mg/kg/day) on days 1 and 3 of PMSG (20 IU) followed 24 hours later by hCG (7 IU). (III) Control group was administrated with PMSG (5 IU), followed by hCG (7 IU) 48 hours later. PEDF prevents edema and ascites (FIGS. 5A-B). FIG. 5A—Development of edema was assessed by the increase in body weight ($\Delta$gr) throughout the treatments. FIG. 5B—Evans blue was injected intravenously 48 hours after hCG administration and peritoneal lavage was performed to collect fluids that leaked into the abdomen. Dye concentration in the fluids was analyzed spectrophotometrically. Bars represent Mean±SEM, 16 mice/treatment. (*)—significantly different from control value ($P<0.05$; two way ANOVA). PEDF inhibits OHSS angiogenesis by regulation of VEGF (FIGS. 5C-D). FIG. 5C—Histological sections of mice ovaries (Control, OHSS and OHSS+PEDF) labeled with CD34 antibody and Hoechst as a nuclear marker. FIG. 5D—qPCR analysis with specific primers against VEGF, calibrated by the endogenous control HPRT1. Bars represent Mean±SEM, 10 mice/treatment, (*)—significantly different from control value ($P<0.05$; two way ANOVA).

Figure 6A:
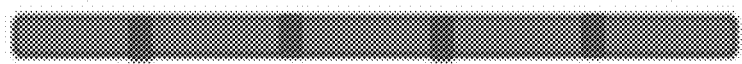
Figure 6B:
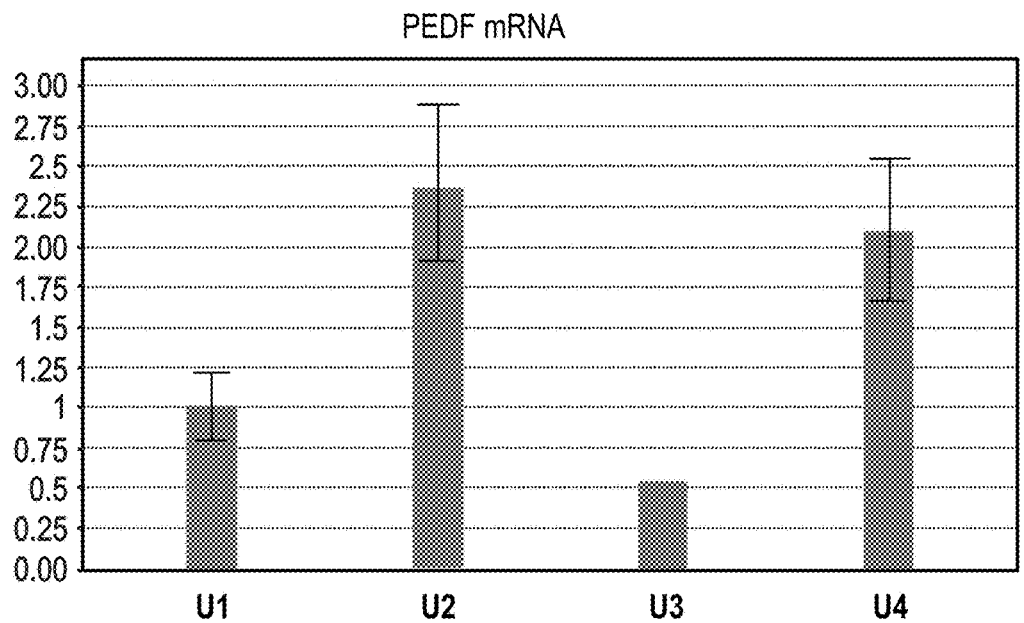
Figure 6C:
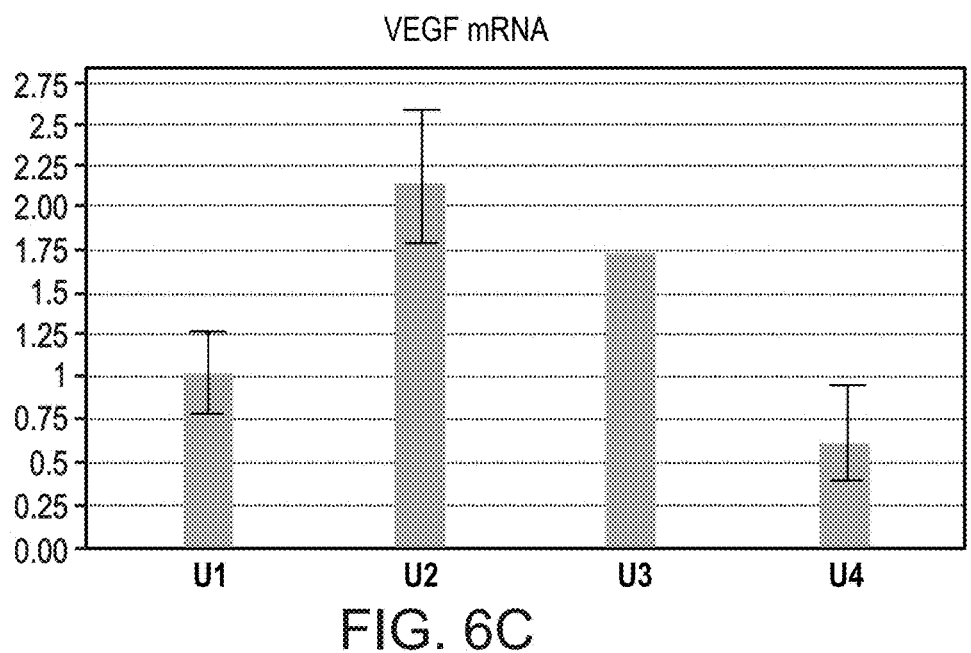

FIGS. 6A-C show PEDF expression in the endometrium during the mouse estral cycle. FIG. 6A—Cartoon illustration of the estrous cycle in the mouse. FIGS. 6B-C—Seven weeks ICR female mice were synchronized by pre-stimulation for superovulation PMSG (5 IU for 48 hr) followed by HCG (7 IU for additional 48 hours). Endometrium samples were collected from day diestrus 2 till disetrus 1 of the next cycle. On each day, 2 mice were scarified and the endometrium layer was subjected to qPCR analysis with Specific primers against PEDF (FIG. 6B) and VEGF (FIG. 6C). Calibration was done with endogenous control HPRT1.

DESCRIPTION OF SPECIFIC EMBODIMENTS OF THE INVENTION

The present invention, in some embodiments thereof, relates to compositions comprising PEDF and uses of same in the treatment and prevention of ovary-related syndromes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

PEDF is an anti-angiogenic factor which is ubiquitously expressed in the body. Despite significant expression in the reproductive system, there is only limited data about PEDF function in the ovary and uterus referring mainly to regulation in cancer.

The present inventors have now uncovered a critical role for PEDF in the regulation of hormonal dependent angiogenesis in the reproductive system and suggest its use in the treatment of a variety of medical conditions of the female reproductive system, especially those associated with infertility.

As is illustrated herein below and in FIGS. 1A-D and 2A-B, the present inventors have found that PEDF is produced in-, and secreted from the granulosa cells. Furthermore, the present inventors have found that gonadotropins as well as steroid hormone stimulation regulate PEDF in an opposite manner to the manner they regulate VEGF. This negative feedback is of much clinical significance as evidenced by animal models of ovarian hyper stimulation syndrome (OHSS) and endometriosis. As shown in FIGS. 4A-D and 5A-D of the Examples section below, the present inventors have shown that recombinant PEDF is a potent treatment for OHSS in a mouse model and further that PEDF/VEGF balance is kept also in the endometrium and is regulated by hormonal changes. All these findings support the use of PEDF in the treatment of medical conditions of the female reproductive system, especially those associated with infertility.

Thus, according to an aspect of the invention there is provided a method of treating or preventing a medical condition selected from the group consisting of ovarian hyperstimulation syndrome (OHSS), endometriosis, infertility and polycystic ovarian syndrome in a subject in need thereof. The method comprising administering to the subject a pharmaceutical composition comprising an active ingredient consisting of pigment epithelium-derived factor (PEDF) and a pharmaceutically acceptable carrier, thereby treating or preventing the medical condition selected from the group consisting of ovarian hyperstimulation syndrome, endometriosis, infertility and polycystic ovarian syndrome in the subject.

As used herein the "subject in need thereof" refers to a mammalian female subject (e.g., human) who is diagnosed and optionally treated for any of the above medical conditions. The subject is typically at the reproductive age, however since PEDF improves the quality of the oocytes it can also be used in the treatment in perimenopause. Veterinary uses are also contemplated.

"Pigment epithelium-derived factor (PEDF)" is also known as serpin F1, EPC-1, cell proliferation inducing gene 35 protein and PIG35. According to a specific embodiment, the PEDF protein refers to the human protein, such as provided in the following GenBank Number M76979.

Since the phosphorylated form of PEDF is a potent anti angiogenic factor, the present invention also contemplates the use of a phosphorylated PEDF (in contrast to non-phosphorylated PEDF) according to the present teachings. PEDF is phosphorylated on 3 distinct sites Ser24 and Ser114 by casein kinase 2 (CK2) and on Ser227 by protein kinase A (PKA). Specifically, contemplated is the use of the triple phosphorylated PEDF. U.S. U.S 20080274967 teaches phosphorylation of PEDF using CK2 and PKA and is fully incorporated herein.

PEDF can be purified as described in Yanagishe et al. 2006 J. Endocrinol. Metab. 91:2447-2450. Alternatively, PEDF is commercially available from Biovendor Inc.

Typically, the medical conditions of the female reproductive system contemplated herein are associated with infertility (e.g., ovulation disorders), oftentimes treated with an ovarian stimulating medication such as further described hereinbelow.

Ovarian stimulating medications are the main treatment modalities for women who are infertile due to ovulation disorders. These medications regulate or induce ovulation. In general, they work like natural hormones—such as follicle-stimulating hormone (FSH) and luteinizing hormone (LH)—to trigger ovulation. Commonly used fertility drugs include:

Clomiphene (Clomid™, Serophene™). This drug is taken orally and stimulates ovulation in women who have polycystic ovary syndrome (PCOS) or other ovulatory disorders. It causes the pituitary gland to release more FSH and LH, which stimulate the growth of an ovarian follicle containing an egg.

Human menopausal gonadotropin, or hMG, (Repronex). This injected medication is for women who don't ovulate on their own due to the failure of the pituitary gland to stimulate ovulation. Unlike clomiphene, which stimulates the pituitary gland, hMG and other gonadotropins directly stimulate the ovaries. This drug contains both FSH and LH.

Follicle-stimulating hormone, or FSH, (Gonal-F, Bravelle™). FSH works by stimulating the ovaries to mature follicles.

Human chorionic gonadotropin, or HCG, (Ovidrel™, Pregnyl™). Used in combination with clomiphene, hMG and FSH, this drug stimulates the follicle to release its egg (ovulate).

Gonadotropin-releasing hormone (Gn-RH) analogs. This treatment is for women with irregular ovulatory cycles or who ovulate prematurely—before the lead follicle is mature enough—during hMG treatment. Gn-RH analogs deliver constant Gn-RH to the pituitary gland, which alters hormone production so that a doctor can induce follicle growth with FSH.

Aromatase inhibitors. This class of medications, which includes letrozole (Femara™) and anastrozole (Arimidex™), is approved for treatment of advanced breast cancer. Doctors sometimes prescribe letrozole for women who don't ovulate on their own and who haven't responded to treatment with clomiphene citrate.

Metformin (Glucophage™). This oral drug is taken to boost ovulation. It's used when insulin resistance is a known or suspected cause of infertility. Insulin resistance may play a role in the development of PCOS.

Bromocriptine (Parlodel). This medication is for women whose ovulation cycles are irregular due to elevated levels of prolactin, the hormone that stimulates milk production in new mothers. Bromocriptine inhibits prolactin production.

Since OHSS typically develops in women suffering from POC, endometriosis and/or unexplained infertility subject to induced ovarian stimulation, treatment with PEDF is contemplated for each of these syndromes alone a combination of same. Thus according to a specific embodiment, the subject may be diagnosed with OHSS, POC and endometriosis.

Specific embodiments of this aspect of the invention are provided infra classified according to the treated medical condition.

OHSS

Infertility among healthy women is a growing phenomenon (about 10% in the United States). Ovarian Hyper Stimulation Syndrome (OHSS) is an exaggerated ovarian response to ovulation-induction therapies, that might develop after hCG administration. The incidence of OHSS in IVF patients is estimated at 3-6% for moderate OHSS and 0.1-2% for severe OHSS. Although rare, OHSS can occur in women undergoing ovulation induction treatment and there have been case reports about spontaneous OHSS in normal cycling women. Therefore the treatment of spontaneous OHSS is also contemplated according to the present teachings. OHSS is associated with facilitated angiogenesis, which results in vascular hyperpermeability, leakage and shift of fluids into extravascular space with consequent clinical manifestations of ascites and hyperviscosity. High Estrogen level serves as a predictor of OHSS. Vascular endothelial growth factor (VEGF) is a crucial protein participating in the syndrome development. VEGF is up-regulated in response to elevated Estrogen level and hCG.

PEDF acts as a strong inhibitor of angiogenesis, known to inhibit the production of pro-angiogenic factors, such as VEGF. PEDF is down-regulated by hCG and high level of Estrogen.

In light of the fact that when OHSS develops, the delicate equilibrium between the pro-angiogenic factor VEGF and the anti-angiogenic factor PEDF in the ovary is shattered PEDF treatment can prevent OHSS onset. Hence, administration of PEDF concomitant with gonadotropins stimulation during the follicular phase is contemplated.

OHSS progression is accompanied by massive and unbalanced angiogenesis. Therefore, treatment of OHSS patients with PEDF during the acute phase will alleviate the symptoms by restoring the angiogenic balance in the ovary.

PCOS

Poly Cystic Ovary Syndrome (PCOS) is the most common endocrine disorder in women of reproductive age. This syndrome may affect 5-10% of premenopausal women. The ovaries of PCOS women are characterized by intense-vascularization, which puts them at high risk of developing OHSS as a result of hormonal treatments. Oocytes of PCOS women are often of poor quality, leading to lower fertilization, cleavage and implantation rates, and to a higher miscarriage rate. VEGF concentration in the serum and ovaries of PCOS women is elevated, compared to non-PCOS, normal ovulating women. Elevated VEGF in follicular fluid of women with PCOS is highly correlated with immature oocytes, poor fertilization rate and development of OHSS. Moreover, the elevated circulating VEGF concentrations in women with PCOS may supply a partial explanation to the presence of the dense hyperechogenic and highly vascularized stroma that is characteristic of a PCOS. It is the intense vascularization that may lead to abnormal growth of the theca interna, which is the site for androgen steroidogenesis.

PEDF acts as a strong inhibitor of angiogenesis, known to inhibit the production of pro-angiogenic factors, such as VEGF.

PEDF administration to PCOS patients undergoing fertility treatment can improve oocytes quality, fertilization and cleavage rates, number of embryos, pregnancy rate and decrease the rate of spontaneous abortions. According to some embodiments of the invention, PEDF is administered before or concomitantly with gonadotropins treatment during the follicular phase. PEDF treatment is also used to overcome the side effects of high androgen levels associated with PCOS, such as acne and excessive hair growth.

Endometriosis

Endometriosis is a pathological condition characterized by ectopic endometrial implants, usually in the peritoneal cavity. Active endometriosis is characterized by hypervascularization both within, and around the implant. Endometriosis is manifested during the reproductive years; it has been estimated that endometriosis occurs in roughly 5-18% of women. Some symptoms may develop at the site of active endometriosis; the main, but not universal symptom is pelvic pain at various manifestations. Other symptoms are: painful sexual intercourse (dyspareunia) or cramping during intercourse, as well as pain during bowel movements and/or urination. Endometriosis is common in women with infertility problems. Endometriosis lesions react to hormonal stimulation by proliferation and angiogenesis. There is a high VEGF level in the peritoneal fluid of patients with endometriosis and its production is stimulated by both Estrogen and Progesterone.

The present inventors have found that PEDF is expressed in the endometrium and that its expression changes throughout the menstrual cycle; this expression is negatively correlated with VEGF expression.

PEDF level in the endometrium is regulated by gonadotropins and steroid sex hormones. It is suggested that PEDF will decrease VEGF level as well as vascularization and hence will alleviate endometriosis-related symptoms. Hence, according to an embodiment of the invention symptomatic women are treated with PEDF. However, since endometriosis is a chronic syndrome which affects every day life, a repetitive administration of PEDF is also contemplated. For example, PEDF may be administered during ferile life span i.e., as long as the ovary secretes the hormones Suggested treatment is in the luteal phase.

Oocyte Quality

Elevated VEGF level in follicular fluid is associated with poor oocyte quality and decreased fertilization and pregnancy rates, especially in older women and PCOS syndrom.

Administration of PEDF will improve oocytes quality in general, such as in perimenopause.

PEDF can be administered to the subject per se, or in a pharmaceutical composition where it is mixed with suitable carriers or excipients.

As used herein a "pharmaceutical composition" refers to a preparation of the active ingredient described herein with other chemical components such as physiologically suitable carriers and excipients. The purpose of a pharmaceutical composition is to facilitate administration of a compound to an organism.

Herein the term "active ingredient" refers to the PEDF accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous, dermal and transdermal and intramedullary (e.g., using injections or patches).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals (as described in the Examples section which follows). The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

Exemplary doses are provided infra:

0.02-0.4 mg/kg 0.162-0.32 mg/kg, 0.01-0.2 mg/kg, 0.1-0.4 mg/kg, 0.2-0.4 mg/kg or 0.05-0.1 mg/kg.

The amount of a composition to be administered will, of course, be dependent on the subject being treated, the severity of the affliction, the manner of administration, the judgment of the prescribing physician, etc.

Thus, the present invention further contemplates a unit dosage form comprising PEDF.

According to a specific embodiment the unit dosage form comprises 1-500 mg PEDF, 1-100 mg PEDF, 1-50 mg PEDF, 1-40 mg PEDF, 1-30 mg PEDF, 1-25 mg PEDF, 9-20 mg PEDF, 1-20 mg PEDF or 10-50 mg PEDF.

The unit dosage form can be in the form of an edible unit dosage form (e.g., a tablet); an injectable unit dosage form e.g., an ampoule for injection, a patch, a pen injector (e.g., prefilled pen cartridges, disposable pen); a unit dosage form for nasal administration (i.e., nasal spray dose unit).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "preventing" refers to keeping a disease, disorder or condition from occurring in a subject who may be at risk for the disease, but has not yet been diagnosed as having the disease.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Materials
Reagents and Buffers:

Pregnant mare's serum gonadotropin (PMSG; Syncropart, Sanofi, Paris, France). Human chorionic gonadotropin (hCG), 17-Beta-Estradiol, progesterone and MII medium were purchased from (Sigma, Rehovot, Israel). Dulbecco's modified Eagle's medium (DMEM/Ham F12 1:1, DMEM-F12) and Dulbecco's PBS were acquired from (DPBS; Biological Industries, Beit-Ha'emek, Israel), fetal calf serum (FCS, Invitrogen, Grand Island, N.Y., USA).

The following antibodies and primers were used:

Primary antibodies: anti-CD34 (CEDARLANE Laboratories, NC), anti-VEGF (abeam, Cambridge UK) anti-PEDF (Santa Cruz Biotechnology, CA), anti-actin (Millipore, Temecula Calif.).

Secondary antibodies: monoclonal Cy3-conjugated, mono and poly clonal HRP-conjugated antibodies (Jackson Immunoresearch, PA, USA). RAT Alexa Fluor 555 conjugated and rabbit Alexa Flour 488 conjugated (Cell signaling technology, MA). DNA were stain using Hoechst 3342 (Sigma, Rehovot, Israel) as a nuclear marker.

TABLE 1

Primers, For PCR

| | | | |
|---|---|---|---|
| Forward 5'CATCCGTA AAGACCTCTATGC-CAAC3 | (SEQ ID NO: 1) | mouse | Actin |
| Reverse 5'CAAAGAAA GGGTGTAAAACGCAGC3' | (SEQ ID NO: 2) | | |
| Forward 5'GTGAAGGT CGGTGTGAACGG3' | (SEQ ID NO: 3) | mouse/ rat | GAPDH |
| Reverse 5'GTGATGGC ATGGACTGTGGTC3' | (SEQ ID NO: 4) | | |
| Forward 5'CATTCACC GGGCTCTCTACTA3' | (SEQ ID NO: 5) | rat | PEDF |
| Reverse 5'TCAGGGGC AGGAAGAAGATGAT3 | (SEQ ID NO: 6) | | |
| Forward 5'TCTCCTTG GCGTGGCTTACTTCAA3' | (SEQ ID NO: 7) | mouse | PEDF |
| Reverse 5'TGCAGAGA CTTGGTAAGTTCGCCT3' | (SEQ ID NO: 8) | | |
| Forward 5'AATTGAGA CCCTGGTGGACA3' | (SEQ ID NO: 9) | mouse/ rat | VEGF |
| Reverse 5'TGAGGTTT GATCCGCATGATC3' | (SEQ ID NO: 10) | | |

TABLE 2

Primers, For qPCR

| | | | |
|---|---|---|---|
| Forward 5'CTCATGGAC TGATTATGGACAGGA3' | (SEQ ID NO: 11) | mouse/ rat | HPRT1 |
| Reverse 5'GCAGGTCAG CAAAGAACTTATAGCC3' | (SEQ ID NO: 12) | | |
| Forward 5'TTCACCCGG AGCAGTGAT3' | (SEQ ID NO: 13) | rat | PEDF |
| Reverse 5'GCCTCCAGA ATTGTGTTTGAG3' | (SEQ ID NO: 14) | | |
| Forward 5'CCAAGTCTC TGCAGGACATGAAG3' | (SEQ ID NO: 15) | mouse | PEDF |
| Reverse 5'GGTTTGCCA GTAATCTTGCTG3' | (SEQ ID NO: 16) | | |
| Forward 5'CTATGCAGA TCATGCGGATCA3' | (SEQ ID NO: 17) | rat | VEGF |
| Reverse 5'TATGCTGCA GGAAGCTCATCTC3' | (SEQ ID NO: 18) | | |

TABLE 2-continued

Primers, For qPCR

| | | | |
|---|---|---|---|
| forward 5'AGGCTGCTG TAACGATGAAGC3' | (SEQ ID NO: 19) | mouse | VEGF |
| Reverse 5'AGGTTTGAT CCGCATGATCTG3' | (SEQ ID NO: 20) | | |

Mouse Model—ICR female mice (5-8 weeks-old; Harlan Laboratories, Jerusalem, Israel) were housed in air conditioned, light controlled animal facilities of the Sackler faculty of medicine. Animal care was in accordance with institutional guidelines and was approved by the local authorities.

Germinal Vesicle (GV) Oocytes—were isolated from ovaries of untreated mice into MII medium [en-Yosef, D., et al., *Tyrosyl-phosphorylated proteins are involved in regulation of meiosis in the rat egg*. Mol Reprod Dev, 1998. 49(2): p. 176-85] supplemented with 1 μM milrinone (Sigma Rehovot, Israel) to prevent resumption of meiosis and maintain oocytes at the GV stage [Barretto, L. S., et al., *Role of roscovitine and IBMX on kinetics of nuclear and cytoplasmic maturation of bovine oocytes in vitro*. Anim Reprod Sci, 2007. 99(1-2): p. 202-7].

Oocytes Arrested at Metaphase of the Second Meiotic Division (Mu)—Female mice were injected with 7 IU of hCG, 48 hours after administration of 5 IU PMSG. Ovulated, cumulus enclosed oocytes were taken from the oviductal ampullae into MI medium, 16-18 hours after hCG administration. Cumulus cells were removed by a brief exposure to 400 IU/ml hyaluronidase (Sigma, Rehovot, Israel).

Mouse OHSS Model—The mouse OHSS model was established as described at [Fainaru, O., M. D. Hornstein, and J. Folkman, *Doxycycline inhibits vascular leakage and prevents ovarian hyperstimulation syndrome in a murine model*. Fertil Steril, 2009. 92(5): p. 1701-5]. Briefly, PMSG (20 IU/day, intraperitoneally (IP)) was administered for 3 days to a 5 weeks old female mice and on forth day, hCG (7 IU, IP) was injected to induce ovulation. The control group was treated with single treatment of PMSG (5 IU) and hCG (7 IU) after 48 hours. Vascular permeability was quantified using the modified Miles vascular permeability assay [Miles, A. A. and E. M. Miles, *Vascular reactions to histamine, histamine-liberator and leukotaxine in the skin of guinea-pigs*. J Physiol, 1952. 118(2): p. 228-57], using Evan's blue dye (Sigma, Rehovot Israel) that binds to plasma proteins and leaks with them at sites of vessel permeability. The abdomen fluid was measured using ELISA reader $OD_{620}$.

Immunofluorescence—GV and MII oocytes were examined. ZP was removed by a brief exposure to alpha-chymotrypsin (50 μg/ml in 1 mM HCl; Sigma, St Louis, Mo.). Oocytes were then fixed by 3% paraformaldehyde (Merck, Gibbstown, N.J.) in DPBS, and washed in a solution of 3% FCS in DPBS (blocking solution). Permeabilization was performed by 10 minutes exposure to 0.05% Nonidet P-40 (NP-40; Sigma, Rehovot, Israel) in blocking solution. Permeabilized oocytes were further incubated for 1.5 hours in the presence of the primary PEDF antibody, washed three times in working solution and incubated for 1 hour with Cy3-conjugated antibody. Photographs were taken, deconvolved, and processed using a Leica laser confocal microscope (Wetzalr, Germany).

Immunohistochemistry—Paraffin-embedded ovarian sections of 5 weeks were deparaffinized and subjected to antigen retrieval by microwave treatment (H-3300; Vector Laboratories, Inc, Burlingame). The sections were cooled on ice to room temperature, rinsed in PBS and incubated for 1 hour with PBSTg (0.2% tween). Subsequently sections were blocked with 2% normal horse serum and incubation overnight with anti-CD34 antibody. For staining with anti-PEDF, sections were rinsed in PBS and incubated for 1 hour with PBSTg (0.2% tween, 0.2% gelatin). After PBS wash, sections were blocked by 10 min incubation in blocking solution (927B; cell marque) and antibody was apply for overnight incubation.

In the following day sections were washed in PBSTg, and PBS before and after applying the appropriate secondary antibodies, sections were rinsed and mounted with moviol (Sigma, Rehovot Israel). Photographs were taken, deconvolved, and processed using using a Leica laser confocal microscope.

Cell Culture

Primary Mouse Granulosa Cells—were isolated from estradiol-primed 27 days old mice. The ovaries were incubated in hypertonic sucrose/EGTA medium and transfer into DMEM-F12 in the presence of indomethacin (10 µM) and follicles were needle-pricked to release granulosa cells. Isolated cells were plated onto serum-precoated 24-multi-well plates (1 ovary per well; Nunc, Copenhagen, Denmark) containing 0.5 ml of DMEM-F12 medium [Orly, J., et al., *Effects of hormones and protein kinase inhibitors on expression of steroidogenic enzyme promoters in electroporated primary rat granulosa cells.* Biol Reprod, 1996. 54(1): p. 208-18].

Primary Human Granulosa Cells—were obtained from women, aged 22-38 years, undergoing IVF treatment in Assaf Harofeh Medical Centre, as of male factor infertility. Patients were treated according to the long protocol guidelines, i.e. received a GnRH agonist at the mid-luteal phase, followed by Follicle Stimulating Hormone (FSH) or human menopausal gonadotropin and eventually by the administration of hCG. Granulosa cells were isolated from aspirated follicular fluid after oocyte retrieval. The follicular fluid was centrifuged at 300 g for 5 min at room temperature. The resulting pellets were re-suspended in 10 mM Tris, 0.84% NH4 Cl, pH 7.4, to lyse blood cells (15 min shaking at 37° C.). Several washings in DPBS eliminated debris. Cells were plated in DMEM-F12, supplemented with penicillin (100 IU/ml, Industries, Beit-Ha'emek, Israel), streptomycin (100 mg/ml, Industries, Beit-Ha'emek, Israel) and 10% FCS. Both primary cultures were incubated for an additional 7 days in medium containing 10% FCS. Before harvesting the cell were serum-starved (0.1% FCS) for 16 hours.

Protein Precipitation—After cells starvation the medium was collected with an equal volume of 10% Trichloroacetic acid (TCA, Sigma, St Louis Mo.) and incubate the mixture for 16 hours in −20πC. The pellet was then washed with ice cold acetone and re-suspend with SDS PAGE loading buffer.

Immunoblotting—Cells were grown to subconfluency and then serum starved (0.1% FCS) for 16 hours. After incubation with indicated treatments, cells were lysed in ice-cold radioimmunoprecipitation assay (RIPA, 20 mM Tris-HCl pH=7.4, 137 mM NaCl, 10% glycerol, 2% NP-40 or 1% triton X-100, 0.5% sodium deoxycholate, 0.1% SDS, 2 mM EDTA pH=8) buffer and extracts were obtained by centrifugation at 15,000×g at 4° C. Precipitated protein was extracted as described above. Aliquots of cellular extracts or precipitated protein were subjected to SDS-PAGE and immunoblotted with the primary antibodies (PEDF, VEGF, and Actin) followed by incubation with the corresponding horseradish peroxidase-conjugated secondary antibody, and developed using Pierce ECL Western Blotting Substrate (Thermo SCIENTIFIC, IL USA).

PEDF Production—Recombinant PEDF was expressed in *E. coli* BL21. Bacterial cells and grown at 30° C. to $OD_{600}$ $nm$=0.5 to 0.6, induced by 0.5 mmol/L isopropyl-L-thio-β-D-galactopyranoside for 4 to 5 hours. Pelleted bacterial cells were lysed, and purification of recombinant proteins was performed using ion metal affinity chromatography with Ni-NTA His-Bind resin (Merck KGaA, Darmstadt, Germany) according to the manufacturer's protocol. Elution fractions were resolved on SDS-PAGE followed by GelCode (Blue Stain Reagent, Thermo SCIENTIFIC, IL USA) or Western blotting using specific anti-PEDF antibody. Eluates that exhibited >90% purity were dialyzed against PBS [Konson, A., S. Pradeep, and R. Seger, *Phosphomimetic mutants of pigment epithelium-derived factor with enhanced antiangiogenic activity as potent anticancer agents.* Cancer Res. 70(15): p. 6247-57].

RNA Isolation, Reverse Transcription (RT), PCR and Real-Time Polymerase Chain Reaction (QPCR)—Total RNA was isolated from tissue or cells using a Trizol reagent according manufacturer instructions (Invitrogen, Grand Island, N.Y., USA), and quantified with the Nano-Drop spectrophotometer (ND-1000; Thermo scientific, MA, USA). First-strand cDNA was created by RT (Maxima™ Reverse transcriptase, Fermentas UAB) from total 1 µg RNA using oligo-dt primers. Alternatively, cDNA was retrieved from 100 oocytes using high sensitive kit (BioRad Reverse Transcription System, Hercules, Calif.). DNA amplification was with 1 µl of the RT reaction and 50 pmol gene-specific primers in ready mix mixture (Sigma, Rehovot, Israel). The number of cycles was determined following pre-testing a range of cycles in which the product showed linear expression (X18, X25, X35, X45). The PCR products were separated by electrophoresis in a 1.5% agarose gel and visualized by ethidium bromide staining. For detecting changes in mRNA expression levels the SYBR green reagent was used (SYBR® Green PCR Master Mix, Carlsbad, Calif., USA) along with 15 ng CDNA and specific primers. The samples were run on ABI Prism 7900 Sequence PCR machine (Applied Biosystems Foster City, Calif., USA).

Example 1

PEDF is Expressed in the Ovary

The ovarian expression of PEDF was analyzed to study its role as an anti angiogenic factor in the ovary. Histological sections of ICR mouse ovaries were immunostained with an anti PEDF antibody (FIG. 1A). PEDF was found to be localized in both the oocytes and their surrounding granulosa cells. PEDF was also found in freshly isolated oocytes at the germinal vesicle (GV) stage and at metaphase of the second meiotic division (MII) (FIG. 1B). Given that PEDF is a secreted glycoprotein and since the communication between the oocyte and its surrounding granulosa cells is bidirectional [17], the origin of PEDF biosynthesis was tested. Interestingly, while PEDF mRNA was expressed in granulosa cells (FIG. 1C), it was not found within the oocytes (FIG. 1D). Hence, it may be that granulosa cells are the source of PEDF production. To further evaluate that, the ability of mouse primary granulosa cells to express and secret PEDF in vitro was analyzed. Mice primary granulosa cells were acquired from 27 days old female mice after 3 days of E2 administration followed by culturing for additional 7 days to reach quiescence. PEDF was detected both in cell lysate and in the culture media (FIG. 2A). In view of the fact that granulosa cells are the source for PEDF biosynthesis and secretion in mouse, the same was analyzed in human granulosa cells can. Human primary granulosa cells were obtained from women undergoing IVF treatments (Helsinki 167/09) pre-cultured for 7 days to reach quiescence. PEDF was found to be abundantly expressed in both culture media and lysates of primary human granulosa cells (FIG. 2B).

To conclude PEDF is ubiquitously expressed in the ovaries and may have an important role in regulation of ovarian angiogenesis.

Example 2

Hormonal Regulation of PEDF Secretion

Given that VEGF is the main pro-angiogenic factor in the ovary [3]), and since VEGF and PEDF were shown to be regulated in an opposite manner in other organs [18], the present inventors have hypothesized that during the menstrual cycle PEDF and VEGF are regulated in an opposite manner, thus allowing the maintenance of coordinated angiogenesis in the ovary.

To explore this hypothesis, the present inventors first collected primary mouse granulosa cells before and after ovulation and looked for changes in mRNA levels of PEDF and VEGF (FIGS. 3A-B). While PEDF was highly expressed in primary granulosa cells, its levels decreased after treatment with LH. VEGF, on the other hand, presented an opposite pattern: no expression before LH stimulation in granulosa cells.

PEDF expression and secretion from human primary granulosa cells were tested in various time intervals from patients' exposure to hCG (FIG. 3E). Furthermore PEDF production increased with time elapse form hCG administration.

Taken together, these findings indicate that while granulosa cells abundantly express PEDF, there is only a low expression of VEGF. After LH stimulation, PEDF production reduces concomitantly with an increase in VEGF expression. The present inventors assumed that this tandem change is of much significance in controlling the ovarian angiogenesis.

The follicular growth is accompanied by gradual production of E2 by granulosa cells, which is known to up regulate VEGF [19, 20]. Furthermore, in contiguity to the LH surge, progesterone picks and remains high to support the CL [21, 22]. Therefore, the present inventors aimed to explore whether E2 and progesterone can regulate PEDF expression. Mouse and human primary granulosa cells were treated with E2 and P and tracked changes in PEDF accumulation in the culture media. Interestingly, stimulation with E2 induced gradual reduction in PEDF where P caused abrupt disappearance of the protein (FIG. 3F-G respectively). These results may imply of sequential regulation of vascularization.

Example 3

PEDF as a Potential Treatment for Ovarian Hyperstimulation Syndrome

It is well established that OHSS is associated with increased VEGF levels which results in vascular hyperpermeability, leakage and shift of fluids into extravascular space [6, 23]. The present results indicate that there is a negative correlation between PEDF and VEGF, implying that in OHSS this balance is disturbed. To test this hypothesis, an OHSS model in mouse was established as described by Fainaru et. al [24] and tracked changes of PEDF and VEGF mRNA in ovarian lysates (FIGS. 4A-B). In mice that developed OHSS VEGF mRNA levels increased as compared to control mice [6], while PEDF levels reduced dramatically.

To verify the role of granulosa cells as the main regulators of the ovarian vasculature the production of VEGF and PEDF mRNAs were compared in two granulose cell populations: those isolated from OHSS model mice and those isolated from control mice (Single administration of 5 IU PMSG and 7 IU hCG, standard superovulation). Concurring with our previous results, granulosa cells from control mice produced smaller amounts of VEGF mRNA than those from OHSS model mice (3 days of PMSG 20 IU stimulation+ single administration of 7 IU hCG). Administration of hCG caused a slight increase in VEGF mRNA in control granulosa cells but a significant up-regulation of VEGF mRNA levels in OHSS granulosa cells (FIG. 4C). On the other hand, PEDF mRNA production was down-regulated by increasing the amount of PMSG while hCG administration had no additive effect (FIG. 4D). These results imply that the excess amount of PMSG reflects an imbalance between the production of the main ovarian pro-angiogenic factor, namely VEGF, and the concomitant dramatic down-regulation of the anti-angiogenic factor, PEDF.

Since it was found that in OHSS, the levels of VEGF are increased concomitantly with decreased levels of PEDF, the ability of PEDF to serve as a potential treatment for OHSS was studied. To test this hypothesis the present inventors injected PEDF in parallel to the excessive administration of gonadotropins, on day 1 and day 3 of PMSG administration whereas injection of PBS served as a control. Changes in weight and peritoneal vascular leakage (quantified using the Miles vascular permeability assay [25]) were monitored. Treatment with high levels of gonadotropins led to two-fold increase in body weight compared to mice treated with regular gonadotropins stimulation (FIG. 5A). PEDF treatment significantly decreased the generalized edema and weight gain which characterizes OHSS.

Importantly, control mice, which were treated with PEDF alone in a similar timetable, did not lose weight (Data not shown). The present inventors then tested whether PEDF decreases peritoneal vascular leakage as well (FIG. 5B). High gonadotropin treatment led to an approximate two fold increase in protein leakage into the abdominal cavity as compared to regular gonadotropins stimulation. PEDF treatment in parallel to the gonadotropin stimulation significantly decreased this leakage (FIG. 5B). Hence, it is possible to conclude that PEDF could serve as a potential therapy for OHSS in a murine model by inhibition of vascular leakage.

OHSS development is characterized by rapid and massive angiogenesis. Therefore, the present inventors examined whether PEDF affects angiogenesis in ovary of OHSS mice model. Ovarian cross sections taken from control, OHSS, and OHSS+PEDF treated mice were stained with CD34 antibody. OHSS mice model exhibited an exaggerated vascularity as compared to control mice (FIG. 5C). Concurrent with the present results, the inventors found that PEDF treatment significantly down-regulated the exaggerated ovarian angiogenesis in OHSS mice model (FIG. 5C).

Finally, the present inventors hypothesized that PEDF-induced inhibition of the overstated angiogenesis is achieved through a direct effect of PEDF on VEGF. In order to examine this hypothesis, mRNA levels of VEGF in OHSS ovaries were analyzed with or without PEDF treatment and compared it to the control group. As described for other systems, PEDF administration reduced VEGF mRNA levels ([18], FIG. 5D).

In view of the above results, it is possible to conclude that treatment with PEDF prevents rapid and over-exaggerated angiogenesis, at least in part, by inhibiting VEGF mRNA production.

Example 4

PEDF in the Endometrium

The above-described results have established a significant role for PEDF as a regulator of angiogenesis in the ovary. Similar to the ovary, the uterine endometrium undergoes cyclic angiogenic changes along the menstrual cycle regulated by pro-angiogenic factors as VEGF [17, 26]. Moreover, it was shown that VEGF is the main regulator of endometrium proliferation and migration and it is regulated by E2 and P [27]. However, as for the ovary, the anti-angiogenic factor is ill defined.

The present inventors aimed to evaluate whether PEDF is expressed in the endometrium and whether it is regulated in a cyclic manner as well. Seven weeks ICR female mice were synchronized by administration of 5 IU PMSG followed by 7 IU hCG 48 hr later. After synchronization, 2 animals were sacrificed each day and changes in PEDF and VEGF mRNA along their next estrous cycle were monitored (FIG. 6A). PEDF was found to be expressed in the endometrium and its expression changed throughout the cycle (FIG. 6B). Interestingly, as in the ovary, PEDF expression is negatively correlated to VEGF (FIG. 6C), suggesting that PEDF might counter-regulate VEGF activity in the endometrium as well.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Reynolds, L. P., S. D. Killilea, and D. A. Redmer, *Angiogenesis in the female reproductive system*. FASEB J, 1992. 6(3): p. 886-92.
2. Moor, R. M. and R. F. Seamark, *Cell signaling, permeability, and microvasculatory changes during antral follicle development in mammals*. J Dairy Sci, 1986. 69(3): p. 927-43.
3. Fraser, H. M., *Regulation of the ovarian follicular vasculature*. Reprod Biol Endocrinol, 2006. 4: p. 18.
4. Redmer, D. A. and L. P. Reynolds, *Angiogenesis in the ovary*. Rev Reprod, 1996. 1(3): p. 182-92.
5. Robinson, R. S., et al., *Angiogenesis and vascular function in the ovary*. Reproduction, 2009. 138(6): p. 869-81.
6. Soares, S. R., et al., *Targeting the vascular endothelial growth factor system to prevent ovarian hyperstimulation syndrome*. Hum Reprod Update, 2008. 14(4): p. 321-33.
7. Chen, S. U., et al., *Signal mechanisms of vascular endothelial growth factor and interleukin-8 in ovarian hyperstimulation syndrome: dopamine targets their common pathways*. Hum Reprod. 25(3): p. 757-67.
8. Lam, P. M. and C. Haines, *Vascular endothelial growth factor plays more than an angiogenic role in the female reproductive system*. Fertil Steril, 2005. 84(6): p. 1775-8.
9. Becerra, S. P., et al., *Pigment epithelium-derived factor behaves like a noninhibitory serpin. Neurotrophic activity does not require the serpin reactive loop*. J Biol Chem, 1995. 270(43): p. 25992-9.
10. Dawson, D. W., et al., *Pigment epithelium-derived factor: a potent inhibitor of angiogenesis*. Science, 1999. 285(5425): p. 245-8.
11. Stellmach, V., et al., *Prevention of ischemia-induced retinopathy by the natural ocular antiangiogenic agent pigment epithelium-derived factor*. Proc Natl Acad Sci USA, 2001. 98(5): p. 2593-7.
12. Tombran-Tink, J., et al., *Organization, evolutionary conservation, expression and unusual Alu density of the human gene for pigment epithelium-derived factor, a unique neurotrophic serpin*. Mol Vis, 1996. 2: p. 11.
13. Petersen, S. V., Z. Valnickova, and J. J. Enghild, *Pigment-epithelium-derived factor (PEDF) occurs at a physiologically relevant concentration in human blood: purification and characterization*. Biochem J, 2003. 374 (Pt 1): p. 199-206.
14. Cheung, L. W., et al., *Pigment epithelium-derived factor is estrogen sensitive and inhibits the growth of human ovarian cancer and ovarian surface epithelial cells*. Endocrinology, 2006. 147(9): p. 4179-91.
15. Pollina, E. A., et al., *Regulating the angiogenic balance in tissues*. Cell Cycle, 2008. 7(13): p. 2056-70.
16. Palmieri, D., J. M. Watson, and C. A. Rinehart, *Age-related expression of PEDF/EPC-1 in human endometrial stromal fibroblasts: implications for interactive senescence*. Exp Cell Res, 1999. 247(1): p. 142-7.
17. Gilchrist, R. B., M. Lane, and J. G. Thompson, *Oocyte-secreted factors: regulators of cumulus cell function and oocyte quality*. Hum Reprod Update, 2008. 14(2): p. 159-77.
18. Cai, J., et al., *Pigment epithelium-derived factor inhibits angiogenesis via regulated intracellular proteolysis of vascular endothelial growth factor receptor 1*. J Biol Chem, 2006. 281(6): p. 3604-13.
19. Shimizu, T., et al., *Differential effect of follicle-stimulating hormone and estradiol on expressions of vascular endothelial growth factor (VEGF) 120, VEGF164 and their receptors in bovine granulosa cells*. J Reprod Dev, 2007. 53(1): p. 105-12.
20. Danforth, D. R., et al., *Vascular endothelial growth factor stimulates preantral follicle growth in the rat ovary*. Biol Reprod, 2003. 68(5): p. 1736-41.
21. Stouffer, R. L., *Progesterone as a mediator of gonadotrophin action in the corpus luteum: beyond steroidogenesis*. Hum Reprod Update, 2003. 9(2): p. 99-117.
22. Shimizu, T. and A. Miyamoto, *Progesterone induces the expression of vascular endothelial growth factor (VEGF) 120 and Flk-1, its receptor, in bovine granulosa cells*. Anim Reprod Sci, 2007. 102(3-4): p. 228-37.

23. Abramov, Y., et al., *Vascular endothelial growth factor plasma levels correlate to the clinical picture in severe ovarian hyperstimulation syndrome.* Fertil Steril, 1997. 67(2): p. 261-5.
24. Fainaru, O., M. D. Hornstein, and J. Folkman, *Doxycycline inhibits vascular leakage and prevents ovarian hyperstimulation syndrome in a murine model.* Fertil Steril, 2009. 92(5): p. 1701-5.
25. Miles, A. A. and E. M. Miles, *Vascular reactions to histamine, histamine-liberator and leukotaxine in the skin of guinea-pigs.* J Physiol, 1952. 118(2): p. 228-57.
26. Ablonczy, Z., et al., *Pigment epithelium-derived factor maintains retinal pigment epithelium function by inhibiting vascular endothelial growth factor-R2 signaling through gamma-secretase.* J Biol Chem, 2009. 284(44): p. 30177-86.
27. Chennazhi, K. P. and N. R. Nayak, *Regulation of angiogenesis in the primate endometrium: vascular endothelial growth factor.* Semin Reprod Med, 2009. 27(1): p. 80-9.

What is claimed is:

1. A method of treating infertility associated with endometriosis in a subject in need thereof, the method consisting of administering to the subject a therapeutically effective amount of pigment epithelium-derived factor (PEDF) and an ovarian stimulating medication, wherein said PEDF is administered subcutaneously, intramuscularly or orally, thereby treating infertility associated with endometriosis in the subject.

2. The method of claim 1, wherein said ovarian stimulating medication comprises gonadotropin stimulation.

3. The method of claim 1, wherein said administering said therapeutically effective amount of PEDF is effected at a dosage range of 0.02-0.4 mg/kg.

4. The method of claim 1, wherein said administering said therapeutically effective amount of PEDF is effected at a dosage range of 0.162-0.32 mg/kg.

5. The method of claim 1, wherein said PEDF is administered prior to said ovarian stimulating medication.

6. A method of treating infertility associated with endometriosis in a subject in need thereof so as to result in a pregnancy, the method consisting of administering to the subject a therapeutically effective amount of pigment epithelium-derived factor (PEDF) and an ovarian stimulating medication, thereby treating infertility associated with endometriosis in the subject.

7. The method of claim 6, wherein said ovarian stimulating medication comprises gonadotropin stimulation.

8. The method of claim 6, wherein said administering said therapeutically effective amount of PEDF is effected at a dosage range of 0.02-0.4 mg/kg.

9. The method of claim 6, wherein said administering said therapeutically effective amount of PEDF is effected at a dosage range of 0.162-0.32 mg/kg.

10. The method of claim 6, wherein said PEDF is administered prior to said ovarian stimulating medication.

\* \* \* \* \*

SEQUENCE LISTING

```
<160> NUMBER OF SEQ ID NOS: 20

<210> SEQ ID NO 1
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 1
catccgtaaa gacctctatg ccaac                                              25

<210> SEQ ID NO 2
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 2
caaagaaagg gtgtaaaacg cagc                                               24

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
rwrdgtgaag gtcggtgtga acgg                                               24

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
gtgatggcat ggactgtggt c                                                  21

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
cattcaccgg gctctctact a                                                  21

<210> SEQ ID NO 6
<211> LENGTH: 22
```

```
<212> TYPE: DNA
<213> ORGANISM: Artificial sequence
<220> FEATURE:
<223> OTHER INFORMATION: Single strand DNA oligonucleotide

<400> SEQUENCE: 6
tcaggggcag gaagaagatg at                                          22

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
tctccttggc gtggcttact tcaa                                        24

<210> SEQ ID NO 8
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 8
tgcagagact tggtaagttc gcct                                        24

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
aattgagacc ctggtggaca                                             20

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
tgaggtttga tccgcatgat c                                           21

<210> SEQ ID NO 11
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 11
ctcatggact gattatggac agga                                        24

<210> SEQ ID NO 12
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 12
```

-continued

```
gcaggtcagc aaagaactta tagcc                                        25

<210> SEQ ID NO 13
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 13
ttcacccgga gcagtgat                                                18

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
gcctccagaa ttgtgtttga g                                            21

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
ccaagtctct gcaggacatg aag                                          23

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
ggtttgccag taatcttgct g                                            21

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
ctatgcagat catgcggatc a                                            21

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
tatgctgcag gaagctcatc tc                                           22

<210> SEQ ID NO 19
<211> LENGTH: 21
<212> TYPE: DNA
<213> ORGANISM: Artificial sequence
```

```
-continued

<220> FEATURE:
<223> OTHER INFORMATION: Single strand DNA oligonucleotide

<400> SEQUENCE: 19
aggctgctgt aacgatgaag c                                               21

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
aggtttgatc cgcatgatct g                                               21
```